(12) United States Patent
Jin et al.

(10) Patent No.: US 12,151,121 B2
(45) Date of Patent: Nov. 26, 2024

(54) SKIN CARE DEVICE

(71) Applicant: LG ELECTRONICS INC., Seoul (KR)

(72) Inventors: Yonggeun Jin, Seoul (KR); Jungkwan Lee, Seoul (KR); Heejung Kim, Seoul (KR); Gueisam Lim, Seoul (KR); Hyoungjun Kim, Seoul (KR); Woohyun Kim, Seoul (KR); Jeongseok Yang, Seoul (KR); Dongwook Moon, Seoul (KR); Mingyu Park, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 364 days.

(21) Appl. No.: 17/597,020

(22) PCT Filed: Jun. 23, 2020

(86) PCT No.: PCT/KR2020/008184
§ 371 (c)(1),
(2) Date: Dec. 22, 2021

(87) PCT Pub. No.: WO2020/262948
PCT Pub. Date: Dec. 30, 2020

(65) Prior Publication Data
US 2022/0314022 A1 Oct. 6, 2022

Related U.S. Application Data

(60) Provisional application No. 62/865,696, filed on Jun. 24, 2019.

(30) Foreign Application Priority Data

Jan. 17, 2020 (KR) ........................ 10-2020-0006593
Jan. 17, 2020 (KR) ........................ 10-2020-0006595

(51) Int. Cl.
*A61N 5/00* (2006.01)
*A61N 5/06* (2006.01)

(52) U.S. Cl.
CPC .... *A61N 5/0616* (2013.01); *A61N 2005/0632* (2013.01); *A61N 2005/0647* (2013.01); *A61N 2005/065* (2013.01)

(58) Field of Classification Search
None
See application file for complete search history.

(56) References Cited

U.S. PATENT DOCUMENTS

2005/0070977 A1* 3/2005 Molina .................... A61N 2/02
607/88
2007/0208395 A1* 9/2007 Leclerc ............... A61N 5/0616
607/86
(Continued)

FOREIGN PATENT DOCUMENTS

| KR | 2020140002760 | 5/2014 |
| KR | 1020160095878 | 8/2016 |

(Continued)

OTHER PUBLICATIONS

PCT International Application No. PCT/KR2020/008184, International Search Report dated Oct. 12, 2020, 3 pages.

*Primary Examiner* — Sana Sahand
(74) *Attorney, Agent, or Firm* — LEE, HONG, DEGERMAN, KANG & WAIMEY

(57) ABSTRACT

A skin care device according to an embodiment of the present disclosure includes an outer case having a first opening, an inner case configured to be fastened to the outer case and having a second opening corresponding to the first opening, and a light output module configured to be accommodated between the outer case and the inner case, in which the light output module includes a module body configured to form a predetermined area based on a shape of the outer (Continued)

case or the inner case, a module cover formed along a part of an outer part of the module body, and, between the module body and the module cover, a plurality of light sources disposed in an array form along the outer part of the module body, and in which each of the plurality of light sources is disposed to face the module body.

11 Claims, 14 Drawing Sheets

(56) References Cited

U.S. PATENT DOCUMENTS

2017/0007846 A1* 1/2017 Rabin .................. A61N 5/0617
2022/0212028 A1* 7/2022 Lee ..................... A61N 5/0616

FOREIGN PATENT DOCUMENTS

| KR | 20170083459 A | * | 7/2017 |
| KR | 1020170083459 | | 7/2017 |
| KR | 101807533 | | 12/2017 |
| KR | 1020190018221 | | 2/2019 |
| KR | 20190121715 A | * | 10/2019 |

* cited by examiner

[Fig. 1]
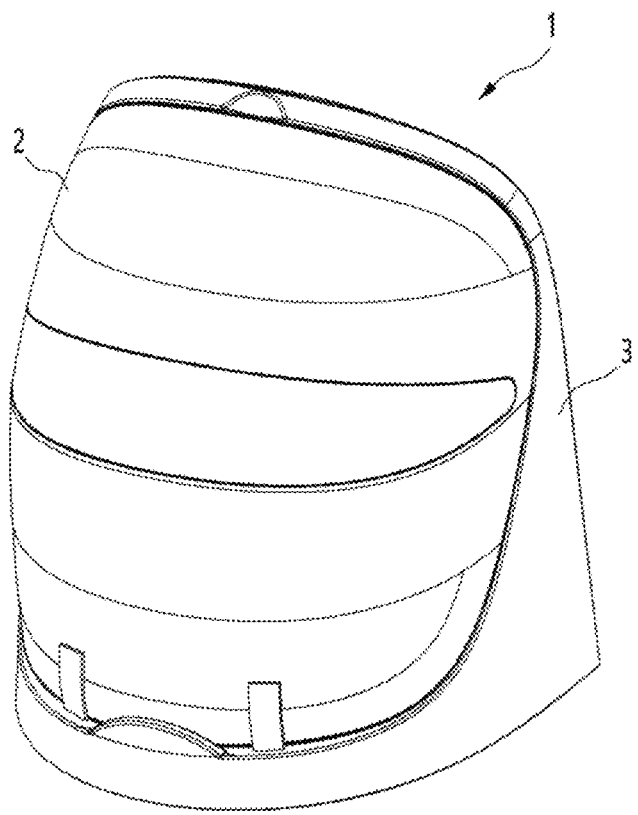

[Fig. 2]
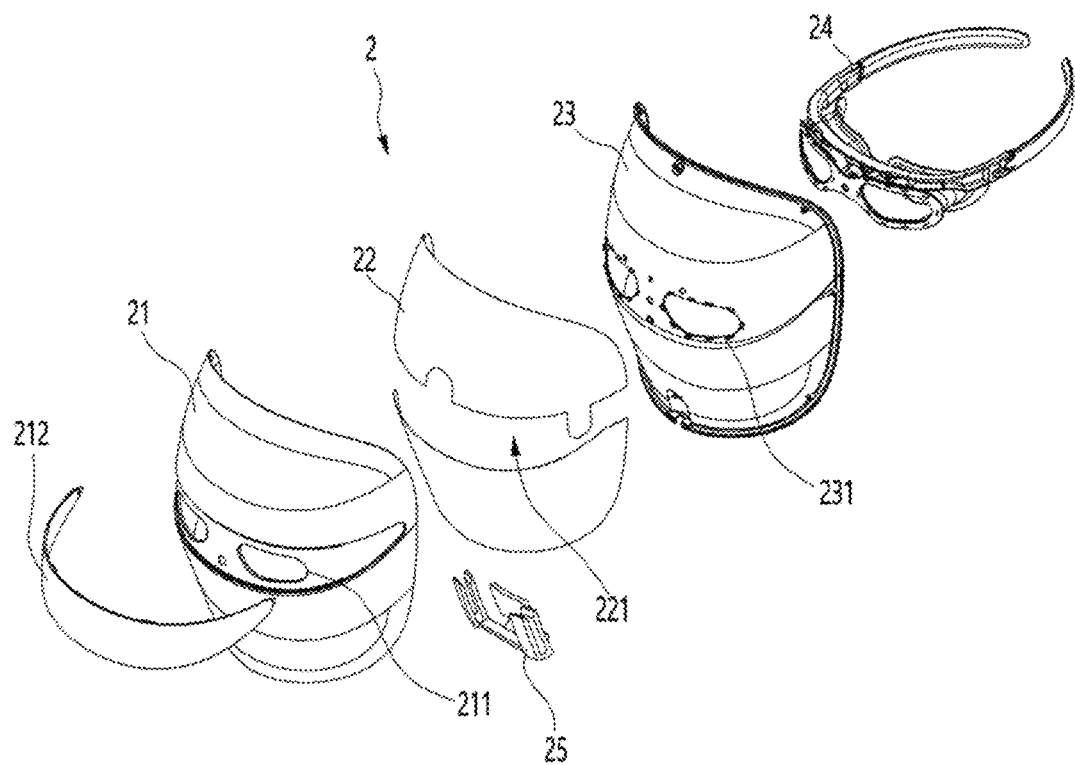

[Fig. 3]
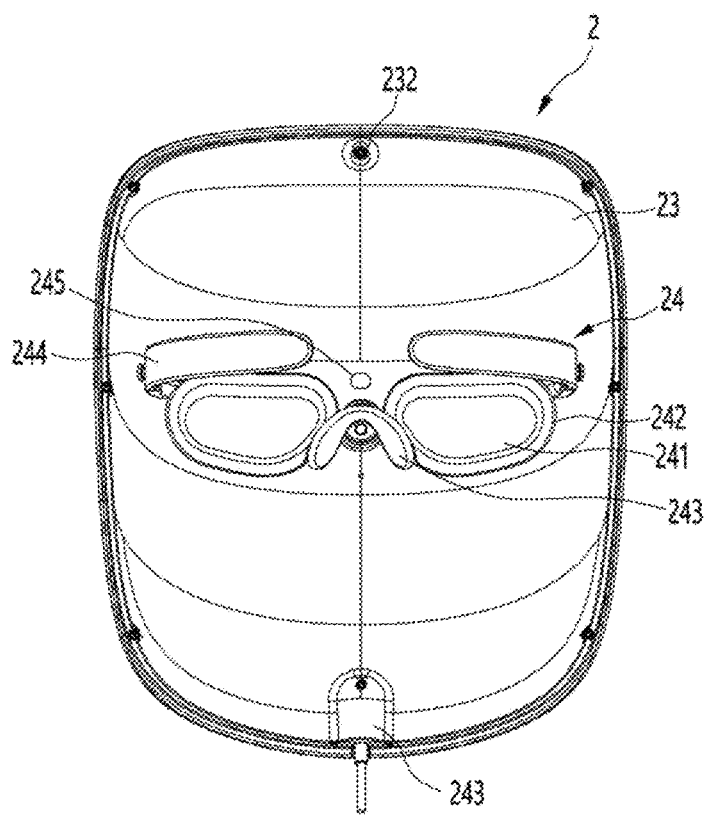

[Fig. 4]
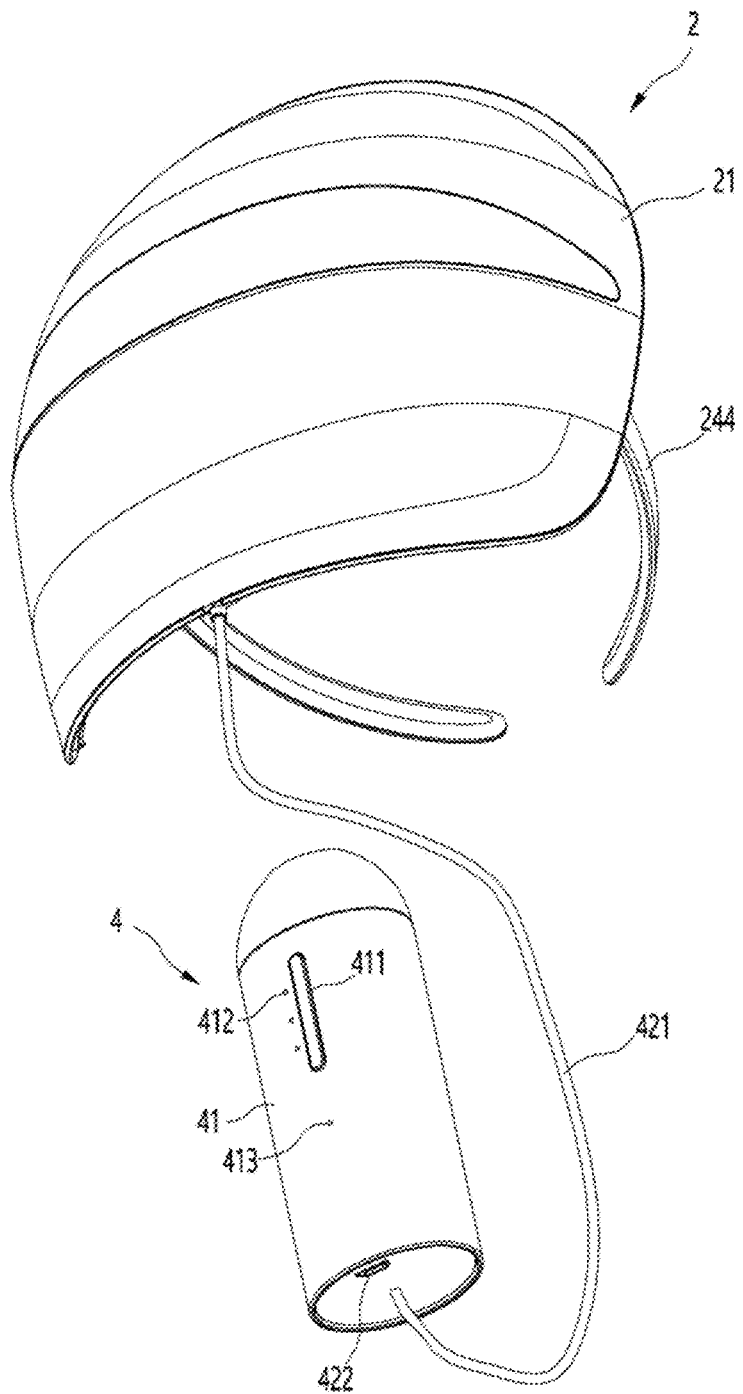

[Fig. 5]
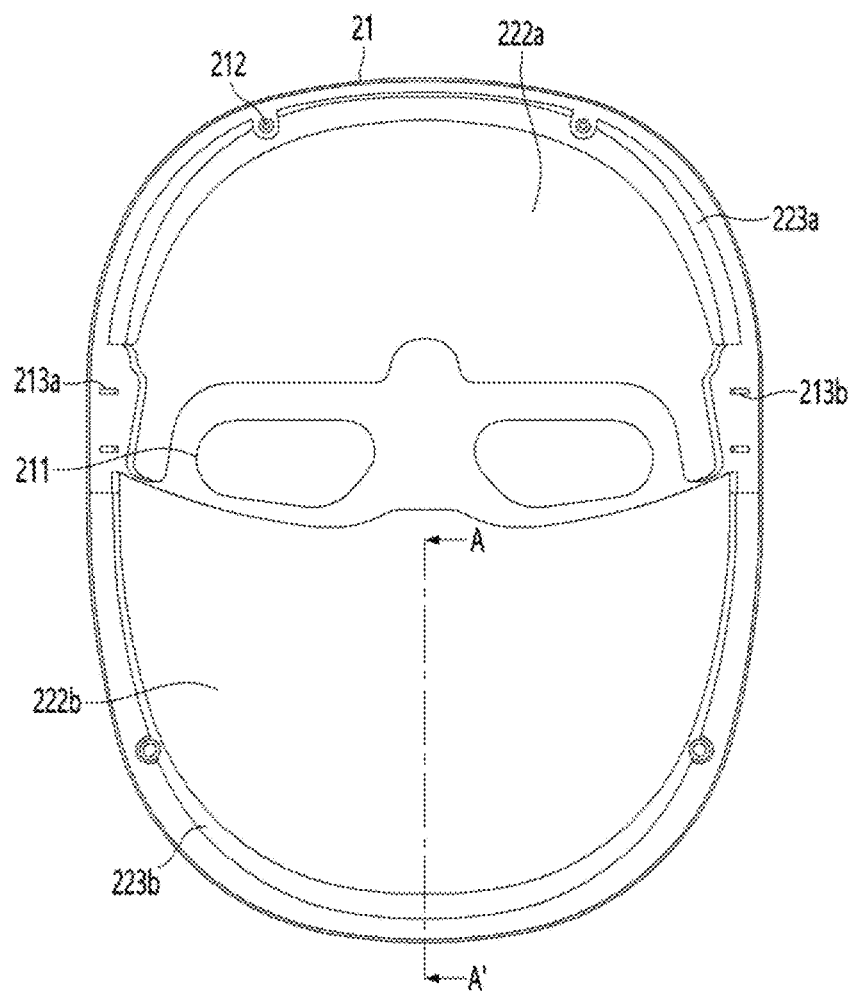

[Fig. 6]
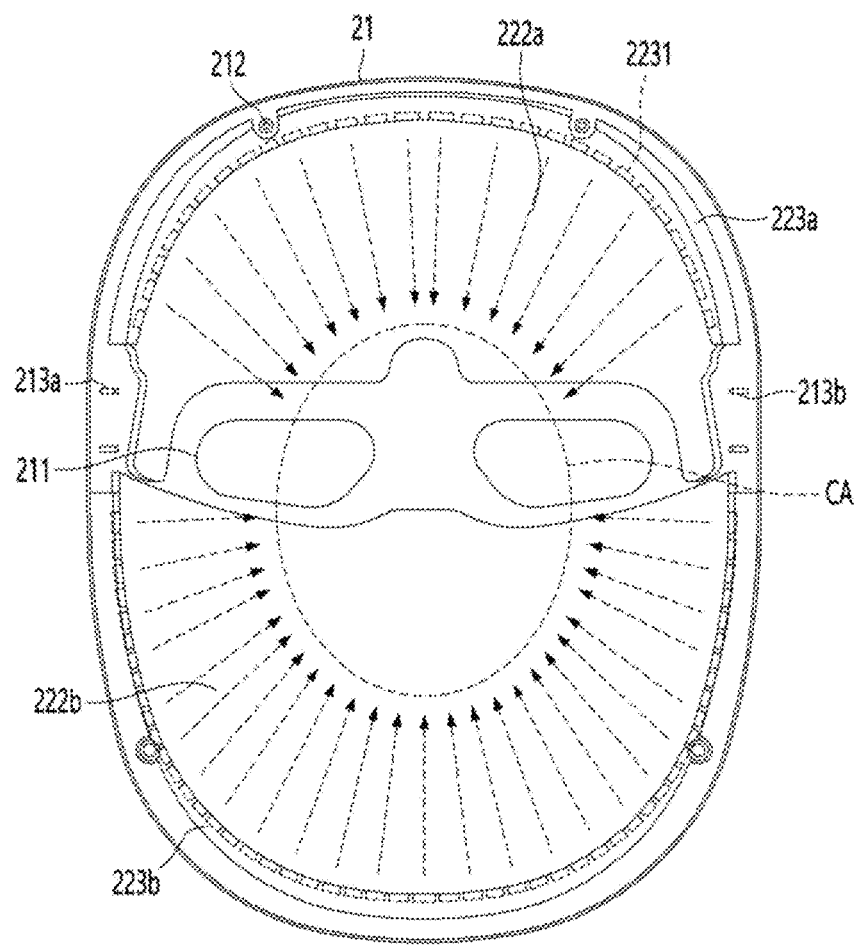

[Fig. 7]
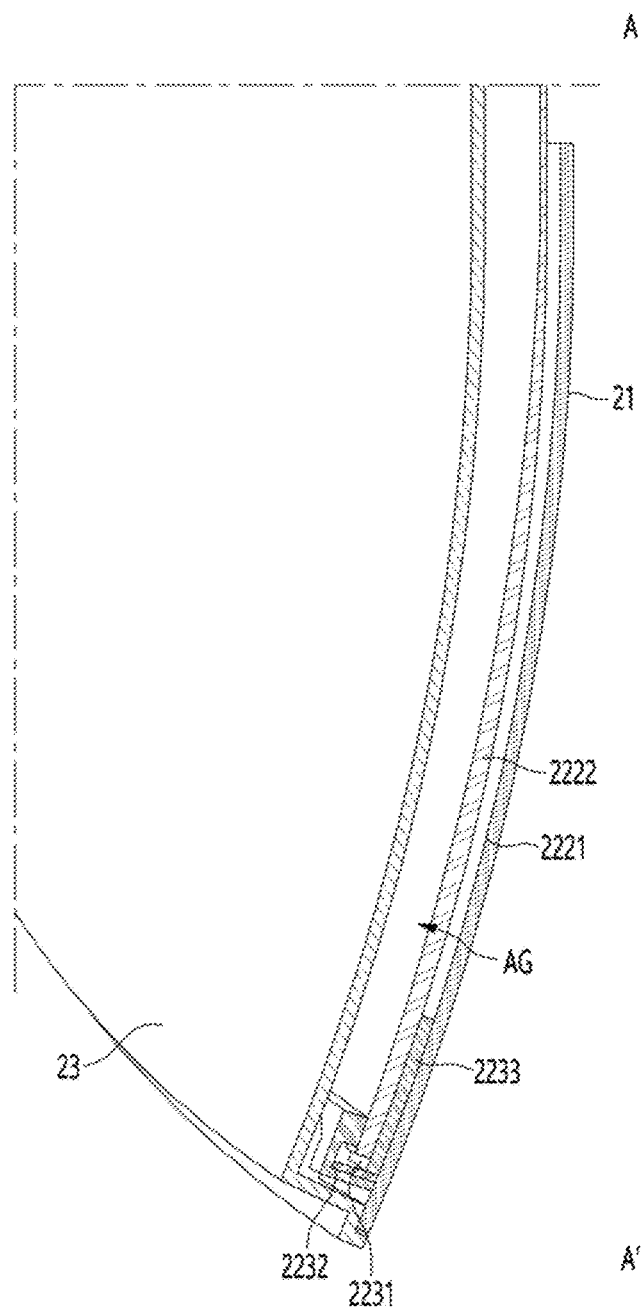

[Fig. 8]
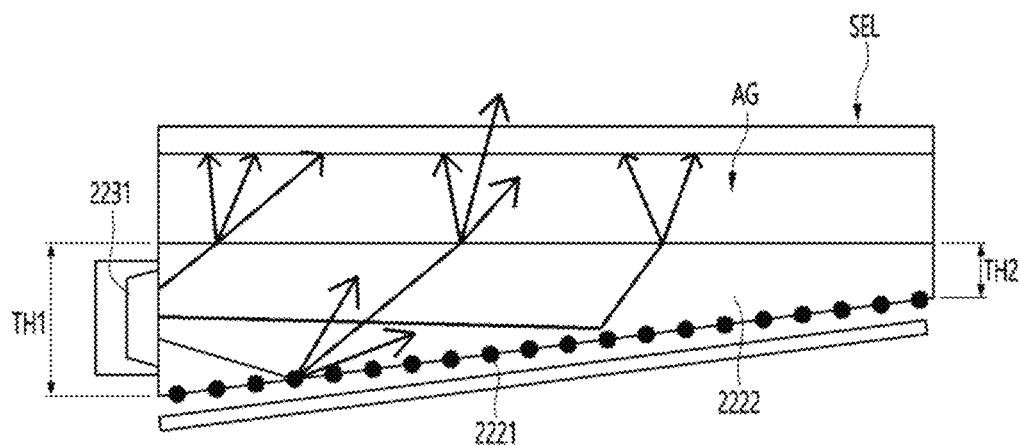

[Fig. 9]
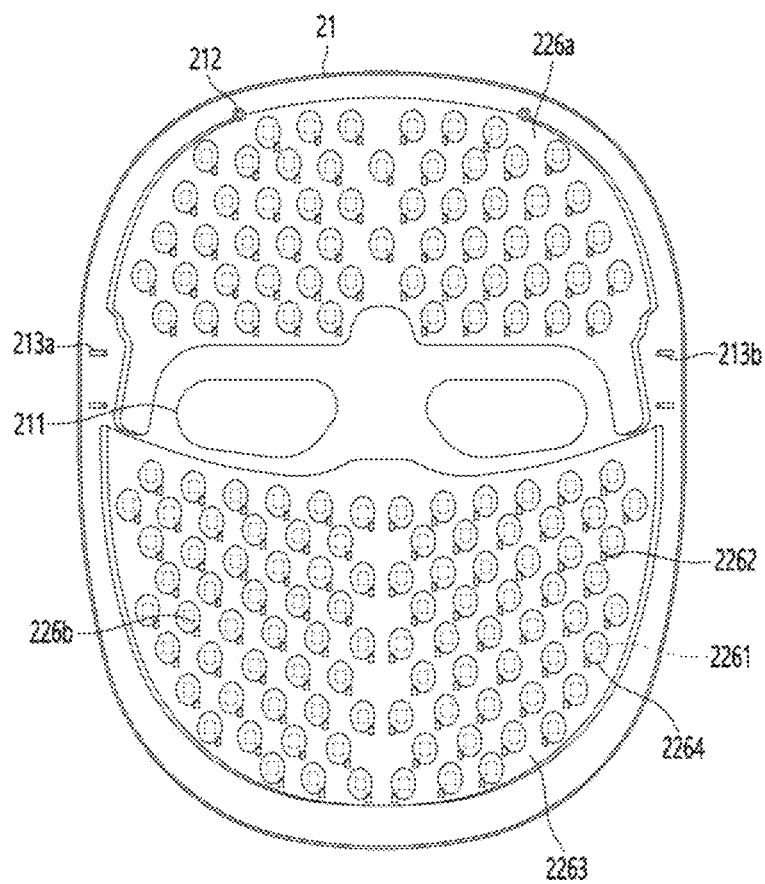
[Fig. 10]
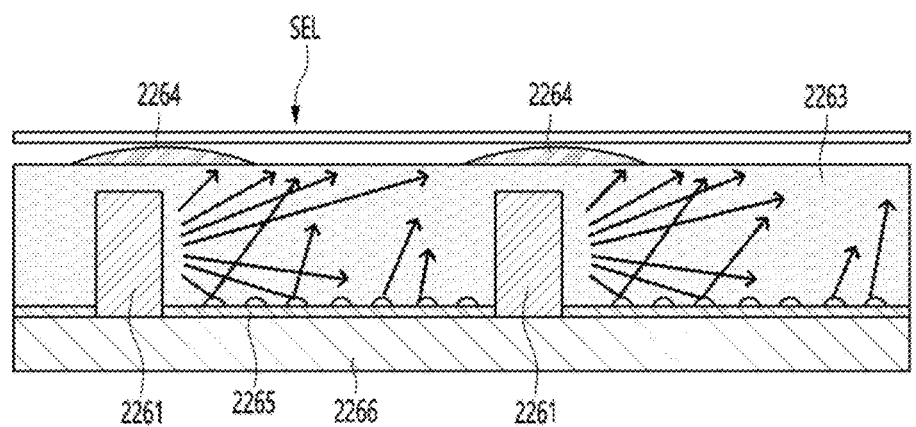

[Fig. 11]
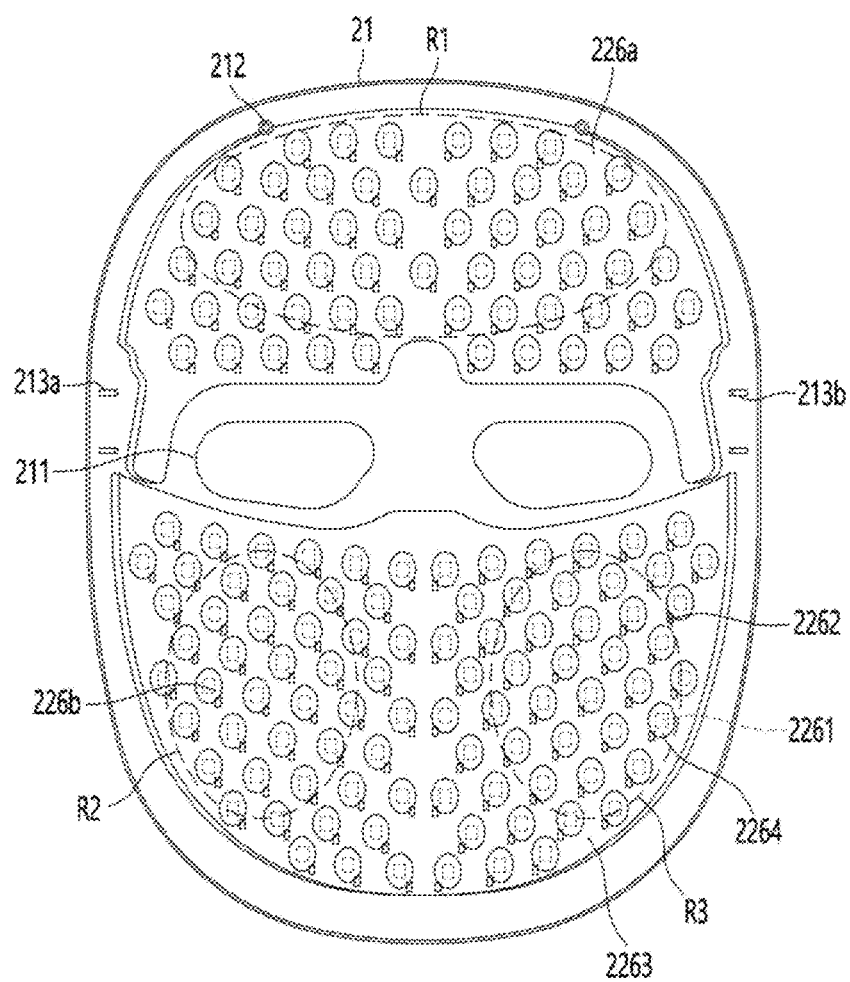

[Fig. 12a]
| Distance (mm) | Light reduction rate(%) | |
|---|---|---|
| | Point light source | Surface light source |
| 0 | 0.0 | 0.0 |
| 5 | 52.9 | 22.5 |
| 10 | 76.5 | 47.3 |
[Fig. 12b]
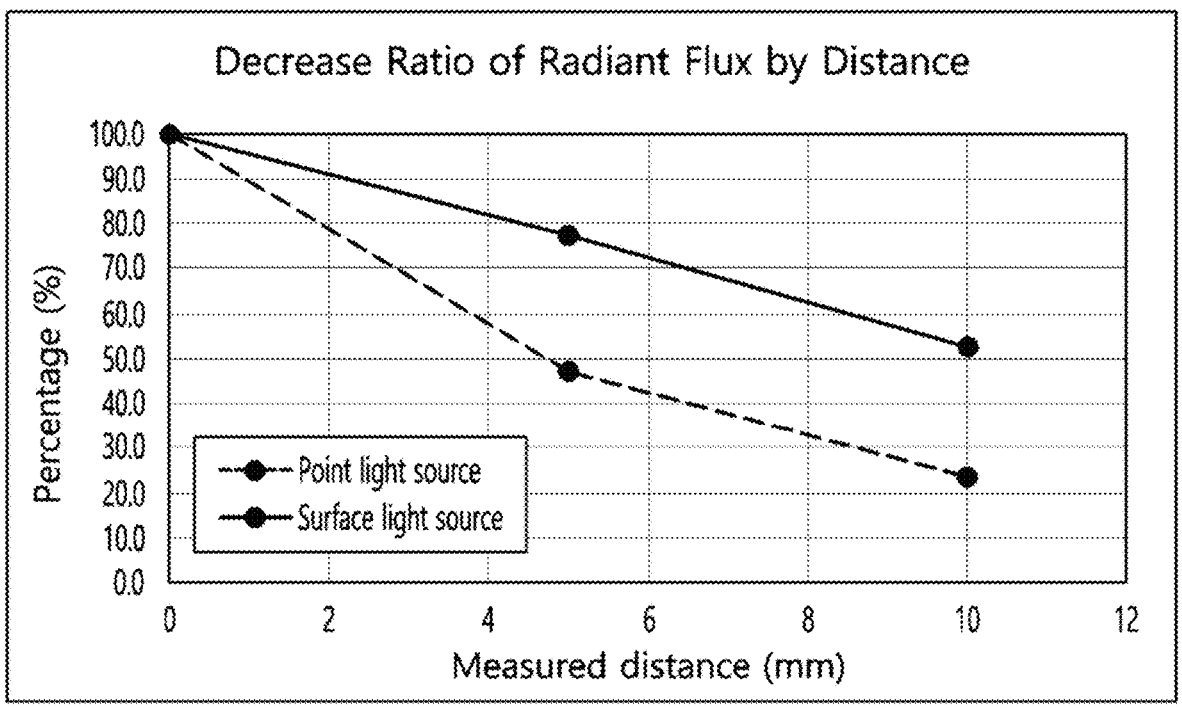

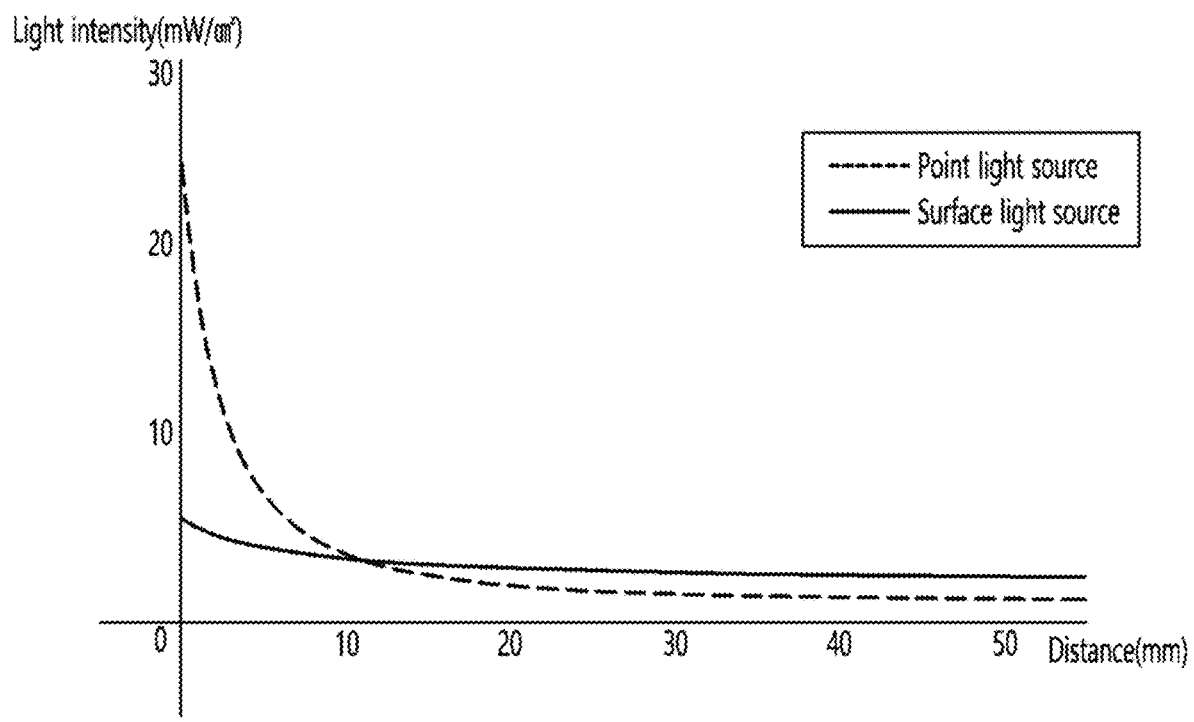
[Fig. 12c]

[Fig. 13a]
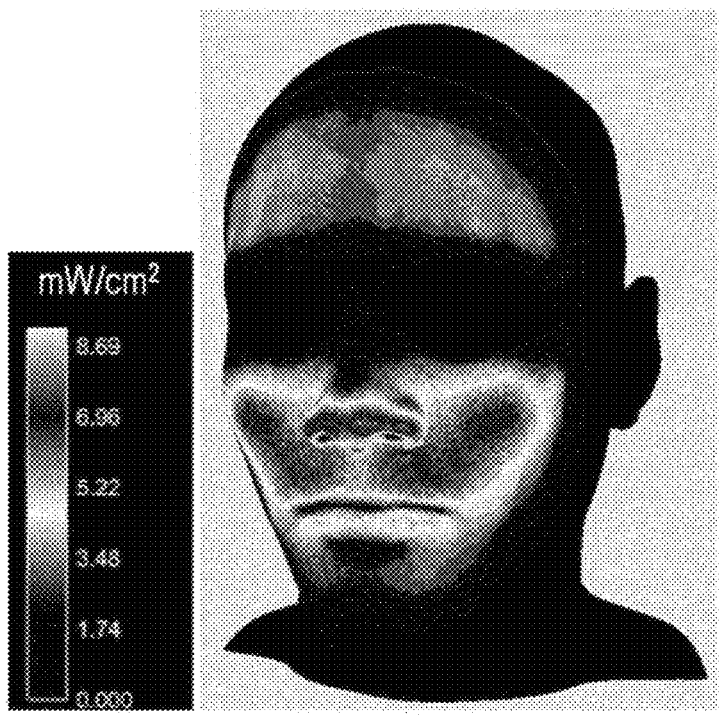

[Fig. 13b]
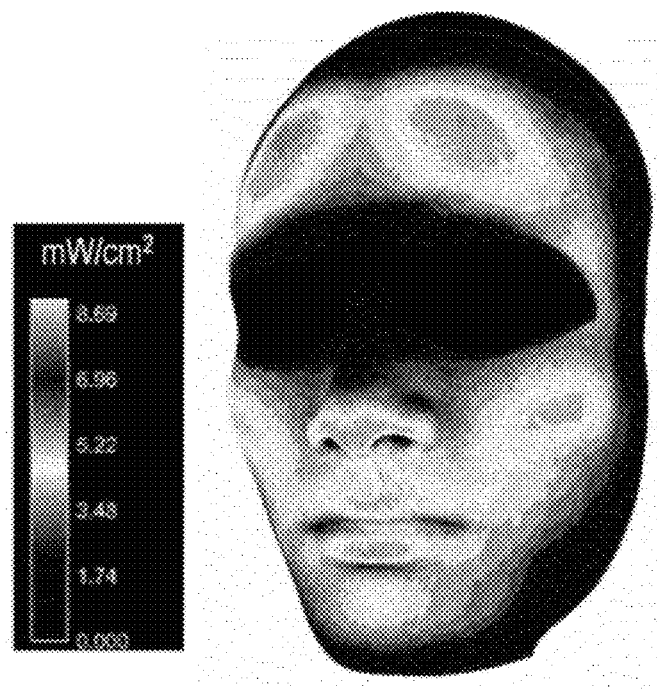

SKIN CARE DEVICE

CROSS-REFERENCE TO RELATED APPLICATIONS

This application is the National Stage filing under 35 U.S.C. 371 of International Application No. PCT/KR2020/008184, filed on Jun. 23, 2020, which claims the benefit of U.S. Provisional Application No. 62/865,696, filed on Jun. 24, 2019, and also claims the benefit of earlier filing date and right of priority to Korean Patent Application Nos. 10-2020-0006593, filed on Jan. 17, 2020, and 10-2020-0006595, filed on Jan. 17, 2020, the contents of all of which are incorporated by reference herein in their entireties.

TECHNICAL FIELD

The present disclosure relates to a skin care device.

BACKGROUND ART

The skin can be damaged due to cell aging, repetition of certain facial expressions, continuous exposure to external environments (UV rays, fine dust, or the like), stress, or the like. For example, aging of cells or repetition of specific facial expressions may cause wrinkles on the skin, and continuous exposure, stress to the external environment, or the like may cause various troubles such as acne and freckles.

Skin care for preventing or minimizing such damage to the skin aims to maintain clean and soft skin without blemishes, and in particular, the most interest is formed in skin care of the face among body parts. Therefore, people want to keep their skin clean by receiving a massage, applying a functional cosmetic product, or using various cleaning products for facial skin care.

In particular, recently, a device (for example, a mask-type skin care device, or the like) that is attached to or worn on a user's face and outputs light for skin care has appeared.

DISCLOSURE

Technical Problem

An object of the present disclosure is to provide a skin care device capable of evenly irradiating light for skin care to skin regions.

Another object to be solved by the present disclosure is to provide a skin care device that minimizes a difference in skin care effects caused by a deviation in distance between the skin care device and skin parts.

Technical Solution

The skin care device according to an embodiment of the present disclosure may include a light output module for outputting light in a surface light-emitting form to a predetermined area of the skin.

According to an embodiment, a skin care device may include an outer case having a first opening, and an inner case configured to be fastened to the outer case and having a second opening corresponding to the first opening, and the light output module may be accommodated between the outer case and the inner case.

According to an embodiment, the light output module may include a module body configured to form a predetermined area based on a shape of the outer case or the inner case, a module cover formed along a part of an outer part of the module body, and, between the module body and the module cover, a plurality of light sources disposed in an array form along the outer part of the module body.

Each of the plurality of light sources may be disposed to face the module body.

According to an embodiment, each of the plurality of light sources may be disposed to face a center of the skin care device or a region of a predetermined size including the center.

According to an embodiment, the module body may include a plate-shaped light guide panel having the predetermined area, and a reflector disposed between the light guide panel and the outer case.

The light guide panel may diffuse and transmit the light emitted from the plurality of light sources and the light reflected from the reflector to the inner case.

The reflector has a curved surface facing the direction in which the plurality of light sources are disposed or an inclined surface at a predetermined angle with respect to the direction in which the plurality of light sources are directed and the light irradiated from the plurality of light sources may be reflected toward the light guide panel.

According to an embodiment, the light guide panel may form different thicknesses according to a separation distance from the plurality of light sources.

According to an embodiment, among the points of the light guide panel, a first thickness of a point at which the separation distance from the plurality of light sources is a first distance may be greater than the second thickness of a point at which the separation distance from the plurality of light sources is greater than the first distance.

According to an embodiment, an air gap region may be formed between the light guide panel and the inner case.

According to an embodiment, the surface of the light guide panel or the surface of the reflector may form an irregular surface.

According to an embodiment, the light output module may include an upper module formed on the upper side with respect to the first opening or the second opening, and a lower module formed on the lower side with respect to the first opening or the second opening, in which a third opening corresponding to the first opening or the second opening may be formed between the upper module and the lower module.

When the skin care device is worn, a distance between the skin care device and the skin may be different for each area.

The light output module may irradiate a surface-emitting form of light having a predetermined area to the outside through the inner case.

According to an embodiment, the light output module may include a substrate and a plurality of light sources disposed on the substrate and facing in a direction parallel to the substrate.

According to an embodiment, each of the outer case, the inner case, and the substrate may form a curved surface having the same or different curvature, and each of the light sources of at least some of the plurality of light sources may face different directions.

According to an embodiment, each of the light sources of at least some of the plurality of light sources may be disposed to face a tangential direction of the substrate.

According to an embodiment, the light output module may further include a reflector formed on at least a portion of a surface facing the inner case among both surfaces of the substrate, and a light diffusion layer formed on the reflector to have a predetermined thickness.

The light diffusion layer may diffuse and transmit light emitted from the plurality of light sources and light reflected from the reflector to the inner case.

According to an embodiment, a thickness of the light diffusion layer may be greater than a height of each of the plurality of light sources from the substrate.

According to an embodiment, the light output module may further include a light transmission amount adjusting layer formed in each of some regions located within a predetermined distance from a plurality of light sources among the surface of the light diffusion layer.

According to an embodiment, the surface of the light diffusion layer or the surface of the reflector may form an irregular surface.

According to an embodiment, an interval or an output of the plurality of light sources may be different depending on whether the plurality of light sources are disposed in the intensive care area.

Advantageous Effect

According to an embodiment of the present disclosure, the skin care device is implemented to irradiate the surface light-emitting form of light to the skin, thereby minimizing the deviation of the irradiated light intensity between the skin regions.

In addition, as the surface light-emitting form of light is irradiated to the skin, it is possible to minimize the deviation of the light intensity due to the difference in the distance between the skin care device and the skin. Accordingly, the skin care device can easily provide a uniform care effect for each skin region.

In addition, since the skin care device having a surface light source according to an embodiment of the present disclosure can provide light with a higher intensity to the skin even with a lower reference light intensity than a conventional skin care device having a point light source, it can maximize the efficiency compared to the skin care device of the prior art.

DESCRIPTION OF DRAWINGS

FIG. 1 is a perspective view illustrating a package including a skin care device and a cradle according to an embodiment of the present disclosure.

FIG. 2 is an exploded perspective view illustrating a skin care device according to an embodiment of the present disclosure.

FIG. 3 is a rear view illustrating a skin care device according to an embodiment of the present disclosure.

FIG. 4 is a perspective view illustrating a skin care device and a user manipulation device according to an embodiment of the present disclosure.

FIG. 5 is a rear view illustrating a light output module of a skin care device according to an embodiment of the present disclosure.

FIG. 6 is a rear view illustrating the light output module illustrated in FIG. 5 in more detail.

FIG. 7 is a schematic cross-sectional view taken in the direction A-A' of FIG. 5.

FIG. 8 is a view for explaining an operating principle of the light output module according to the embodiment of FIG. 5.

FIG. 9 is a rear view illustrating a light output module of a skin care device according to an embodiment of the present disclosure.

FIG. 10 is a cross-sectional view illustrating the light output module illustrated in FIG. 9.

FIG. 11 is an exemplary view for explaining an embodiment related to the arrangement of the light source of the light output module illustrated in FIG. 9.

FIGS. 12a to 12c are experimental data for explaining a change in a light reduction rate according to a separation distance for a point light source and a surface light source, respectively.

FIG. 13a is an exemplary view illustrating the intensity of light irradiated to skin regions when a skin care device equipped with a point light source is used, and FIG. 13b is an exemplary view illustrating the intensity of light irradiated to the skin regions when a skin care device equipped with a surface light source is used.

BEST MODE

Hereinafter, the embodiments disclosed in the present specification will be described in detail with reference to the accompanying drawings, but the same or similar components are assigned the same reference numerals regardless of reference numerals, and overlapping descriptions thereof will be omitted. The suffixes "module" and "part" for the components used in the following description are given or mixed in consideration of only the ease of writing the specification, and do not have distinct meanings or roles by themselves. In addition, in describing the embodiments disclosed in the present specification, if it is determined that detailed descriptions of related known technologies may obscure the subject matters of the embodiments disclosed in the present specification, the detailed description thereof will be omitted. In addition, it should be understood that the accompanying drawings are only for easy understanding of the embodiments disclosed in the present specification, and the technical spirit disclosed herein is not limited by the accompanying drawings, and all changes, equivalents, and substitutes included in the spirit and the technical scope of the present disclosure are included.

Terms including an ordinal number, such as first and second, may be used to describe various components, but the components are not limited by the terms. The above terms are used only for the purpose of distinguishing one component from another.

When a component is referred to as being "connected" or "accessed" to another component, it should be understood that the component may be directly connected or accessed to another component, but there may be other components in between. On the other hand, when it is said that a component is "directly connected" or "directly accessed" to another element, it should be understood that there are no other component in between.

The singular expression includes the plural expression unless the context clearly dictates otherwise.

It should be understood that, in the present application, terms such as "comprises" and "have" are intended to designate that a feature, number, step, operation, component, part, or combination thereof described in the specification exists, but this does not preclude the possibility of the existence or addition of one or more other features, numbers, steps, operations, components, parts, or combinations thereof.

Hereinafter, embodiments of the present disclosure will be described in detail with reference to the accompanying drawings in the present specification.

FIG. 1 is a perspective view illustrating a package including a skin care device and a cradle according to an embodiment of the present disclosure, FIG. 2 is an exploded perspective view illustrating a skin care device according to an embodiment of the present disclosure, FIG. 3 is a rear view illustrating a skin care device according to an embodiment of the present disclosure, and FIG. 4 is a perspective view illustrating a skin care device and a user manipulation device according to an embodiment of the present disclosure.

Referring to FIG. 1, the skin care device 2 may be worn on a part of the user's body and output light to the user's skin. Accordingly, the skin care device 2 may perform skin care operations such as improving wrinkles, elasticity, and skin tone by promoting the activation of the user's skin cells. The skin care device 2 may constitute one skin care package 1 together with the cradle 3 mounted when the skin care device 2 is charged or stored. As a battery (not illustrated) provided in the skin care device 2 is mounted on the cradle 3, the battery may be charged by power supplied from the cradle 3.

The skin care device 2 according to an embodiment of the present disclosure may correspond to a mask type device that is worn on the user's face and outputs light to the user's facial skin, but is not limited thereto. In this case, the skin care device 2 may be formed to be generally rounded according to the shape of a person's face.

The cradle 3 is connected to the skin care device 2 and can supply power for charging with a battery (not illustrated) provided in the skin care device 2 or a user manipulation device 4 (refer to FIG. 4) connected to the skin care device 2. To this end, the cradle 3 may be connected to an external power supply to receive power from the outside.

The cradle 3 may form a seating portion for the skin care device 2 to be seated thereon. As illustrated in FIG. 1, the cradle 3 may have a seating portion formed to correspond to the outer edge of the skin care device 2, but this is not necessarily the case.

Referring to FIG. 2, the skin care device 2 may include an outer case 21, a light output module 22, an inner case 23, and a wearing device 24. When the user wears the skin care device 2, the outer case 21 may face the outside, and the inner case 23 may face the user's face.

The outer case 21 forms one surface (hereinafter, referred to as the front surface) of the skin care device 2, and the optical output module 22 provided between the inner case 23 and the outer case 21 can be protected from the external shock, contact, or the like. To this end, the outer case 21 may be implemented with a material such as plastic or ceramic.

An opening 211 may be formed in the outer case 21 to secure a view of the user when worn by the user. When the user wears the skin care device 2, the user's eyes are positioned in the opening 211, so that the user can secure a view through the opening 211. In some embodiments, an opening protection cover 212 covering the opening 211 may be provided in order to prevent foreign substances from coming into contact with or colliding with the user's eyes through the opening 211. The opening protective cover 212 may be implemented with a transparent material such as acrylic and plastic.

The light output module 22 may be implemented to irradiate the skin with light for user's skin care. For example, the light output module 22 may include a plurality of red light sources and a plurality of infrared light sources. The light source may be implemented as a light emitting diode (LED).

According to an embodiment, in order to output light of different colors according to the operation mode of the skin care device 2, the light output module 22 may include a plurality of LEDs that output light of different colors. For example, the plurality of LEDs may include at least one red LED and at least one blue LED. A red LED may emit red light with a wavelength of about 630 nm to 670 nm. Red light promotes the activity of skin cells, so the red light can be effective in improving wrinkles, elasticity, and skin tone. A blue LED may emit blue light with a wavelength of about 400 nm to 430 nm. Blue light can be effective in removing various skin troubles.

Assuming that the operation mode of the skin care device 2 is divided into an active promotion mode and a trouble removal mode, when the operation mode is set to the active promotion mode, the red LED may be activated to emit red light to the skin. On the other hand, when the operation mode is set to the trouble removal mode, the blue LED may be activated to emit blue light to the skin. According to an embodiment, the plurality of LEDs may further include at least one yellow LED. The yellow LEDs can emit yellow light with a wavelength of about 580 nm to 600 nm, and the yellow light can be effective in brightening skin tones.

The light output operation of the light output module 22 may be controlled by a processor included in a user manipulation device 4 to be described later. The processor may be implemented as an integrated circuit (IC), a microcomputer, an embedded processor, an application processor (AP), or the like.

Meanwhile, the light output module 22 according to an embodiment of the present disclosure may be implemented as a surface light source module. In other words, the light output module 22 irradiates light to the skin regions in a surface light-emitting form, so that the light can be evenly irradiated to the skin regions. A detailed structure of the light output module 22 according to an embodiment of the present disclosure will be described later with reference to FIGS. 5 to 11.

Similar to the outer case 21, an opening 221 may be formed in the light output module 22 to secure a view when worn by the user. As described above, when the user wears the skin care device 2, the user's eyes are positioned in the opening 221, so that the user can secure a view through the opening 221.

Meanwhile, at least a portion of the light output module 22 provided in the skin care device 2 having a mask shape may be formed to have a curved surface. To this end, the substrate provided in the light output module 22 may be implemented as an FPCB or the like to have a curved shape.

The inner case 23 may form a rear surface of the skin care device 2. The inner case 23 may be fastened to the outer case 21 by the fastening member 232 (refer to FIG. 3) to cover one surface of the light output module 22. The outer case 21 and the inner case 23 prevent water or other foreign substances from penetrating into the light output module 22 disposed therein, so that failure or damage of the light source or other components provided in the light output module 22 can be prevented.

In addition, in a case where the user wears the skin care device 2, the inner case 23 is positioned between the light output module 22 and the user's skin to prevent the user's skin from directly contacting the light output module 22.

The inner case 23 may be made of transparent or translucent plastic or acryl, so that the light emitted from the light output module 22 is irradiated to the user's skin.

The inner case 23 may also include an opening 231 for securing a user's view, like the outer case 21 and the light output module 22.

The wearing device 24 may fix the skin care device 2 to the user as the user wears the skin care device 2. The wearing device 24 may be fastened to the outer case 21 and/or the inner case 23. For example, the wearing device 24 may have a shape of glasses that can be worn while being seated on the user's nose and ears.

In particular, the wearing device 24 according to an embodiment of the present disclosure may include a wear detection sensor for effectively detecting whether the user is wearing the wearing device. A more specific structure and configuration of the wearing device 24 will be described later with reference to FIG. 3.

According to an embodiment, a chin fixing device 25 may be provided under the skin care device 2. The chin fixing device 25 may be detachably coupled to at least one of the outer case 21 and the inner case 23. The chin fixing device 25 can stably fix the skin care device 2 to the user's face by being in contact with the user's chin when the user wears the skin care device 2.

Referring to FIG. 3, the wearing device 24 may include an opening 241, a face contact part 242, a nose seating part 243, a wearing fixing part 244, and a wearing detection sensor 245.

Like the outer case 21, the light output module 22, and the inner case 23, the opening 241 may be formed to secure a view when worn by the user. The opening 241 may include a first opening and a second opening formed at positions corresponding to the left and right eyes of the user, respectively. According to an embodiment, in a case where the opening protective cover 212 is not provided in the outer case 21, a lens may be provided in the opening 241 of the wearing device 24. By the opening protective cover 212 or the lens, it is possible to prevent foreign substances from coming into contact with or collide with the user's eyes.

Comparing the openings formed in each of the outer case 21, the light output module 22, the inner case 23, and the wearing device 24 with each other, the size of the opening 221 formed in the light output module 22 may be greater than or equal to the size of the remaining openings 211, 231, and 241. In other words, the boundary surface of the opening 221 formed in the light output module 22 is spaced apart from the user's left and right eyes by a predetermined distance, thereby preventing the surface light source of the light output module 22 from being disposed close to the user's left and right eyes. Meanwhile, the size of the opening 241 formed in the wearing device 24 is formed to be smaller than or equal to the size of the other openings 211, 221, and 231 to effectively secure the user's view.

The face contact part 242 may be formed along the boundary surface of the opening 241. In a case where the user wears the skin care device 2, the face contact part 242 may be composed of a first face contact part and a second face contact part which respectively contact the skin surface located around the user's left eye and the skin surface located around the right eye of the user. As the face contact part 242 comes into contact with skin surfaces located around both eyes of the user, it is possible to prevent the light emitted from the light output module 22 from being irradiated to the user's eyes. The face contact part 242 may be made of a material such as rubber and silicon and may have an opaque color that minimizes light transmission.

The nose seating part 243 may be disposed between the first opening and the second opening or between the first face contact part and the second face contact part and may be seated on the user's nose when worn by the user. In order to be seated on the user's nose, the nose seating part 243 may be formed to be rounded to correspond to the shape of a person's nose.

The wearing fixing part 244 may be fixed to the user's body by being seated on the user's ear or in close contact with the user's head circumference when worn by the user. By the nose seating part 243 and the wearing fixing part 244, the skin care device 2 may be worn and fixed on the user's body.

The wear detection sensor 245 may detect whether the skin care device 2 is worn on the user's body. For example, the wear detection sensor 245 may be implemented as a proximity sensor. When the wear detection sensor 245 is implemented as a proximity sensor, the proximity sensor may detect that a part of the user's body (for example, face) approaches the proximity sensor as the skin care device 2 is worn. The proximity sensor may transmit a detection signal according to detection of proximity of a user's body part to a processor (for example, a processor of the user manipulation device 4). The processor may detect whether the skin care device 2 is worn based on a detection signal transmitted from the proximity sensor.

According to an embodiment, when the user wears the skin care device 2, in a case where the processor continuously receives a detection signal from the wear detection sensor 245 for a predetermined time or more in order to prevent erroneous detection due to proximity of other parts such as the user's hand, the processor may detect that the skin care device 2 is normally worn.

The wear detection sensor 245 may be electrically connected to the light output module 22 or may also be electrically connected to the user manipulation device 4 through the light output module 22.

In particular, as illustrated in FIG. 3, the wear detection sensor 245 may be disposed between the first opening and the second opening, or between the first face contact part and the second face contact part, and above the nose seating part 243. In other words, the wear detection sensor 245 may be positioned to correspond to the forehead or an middle of the forehead when worn by the user and may detect the proximity of the user's forehead or the middle of the forehead.

A person's face shape may be different from each other, and the distance between the skin care device 2 and each part of the face may also be partially different according to the face shape. However, in general, when the skin care device 2 is worn, the distance between the skin care device 2 and the middle of the forehead may have a relatively small difference according to the face shape. Accordingly, in the skin care device 2 according to an embodiment of the present disclosure, the wear detection sensor 245 is disposed at a position corresponding to the user's the middle of the forehead, thereby more effectively detecting whether the user is wearing the skin care device 2 regardless of the user's face shape.

Referring to FIG. 4, the package 1 may further include a user manipulation device 4. The user manipulation device 4 may be connected to the skin care device 2 by wire through a cable 421, but this is not always the case and may be connected wirelessly through a wireless communication method. In this case, each of the light output module 22 of the skin care device 2 and the user manipulation device 4 may further include a wireless communication chip or an element.

The user manipulation device 4 may provide an interface for allowing the user to turn on/off the power of the skin care device 2 or setting an operation mode of the skin care device 2.

At least one button 411 may be provided on the main body 41 of the user manipulation device 4. For example, the at least one button 411 may include a power button for turning on/off the power of the skin care device 2 and an operation mode button for changing an operation mode of the skin care device 2. As illustrated in FIG. 4, the at least one button 411 may be integrally formed with a power button and an operation mode button. In this case, one side of the button 411 may correspond to the power button, and the other side thereof may correspond to the operation mode button. According to an embodiment, the at least one button 411 may include a power button and an operation mode button separated from each other. The user may turn on/off the power of the skin care device 2 or set an operation mode of the skin care device 2 through a manipulation such as the press of the button 411.

The user manipulation device 4 may include an operation mode display part 412 providing information on the currently set operation mode according to the manipulation of the button 411, and a battery information display part 413 providing information related to the battery state. The operation mode display part 412 and the battery information display part 413 may be implemented as LED light sources, but this is not necessarily the case.

Specifically, the operation mode display part 412 may notify the user of information on the currently selected operation mode. To this end, the operation mode display part 412 may include a plurality of operation mode display parts. For example, it is assumed that the plurality of operation modes include an activation promoting mode for improving wrinkles, elasticity, and/or skin tone of the skin, and a trouble removing mode for removing skin troubles. In this case, the first operation mode display part among the plurality of operation mode display parts may correspond to the activation promotion mode, and the second operation mode display part may correspond to the trouble removal mode. In other words, in a case where the currently selected operation mode is the active promotion mode, the first operation mode display part is activated to output light of a specific color (for example, red light), and in a case where the currently selected operation mode is the trouble removal mode, the second operation mode display part may be activated to output light of a specific color (for example, blue light).

The battery state display part 413 may visually provide information related to the remaining amount of the battery to the user. For example, based on the remaining amount of the battery, the color of the battery state display part 413 may be changed or the blinking cycle or the like may be changed.

For example, in a case where the remaining amount of the battery is equal to or greater than the reference amount, the color of the battery state display part 413 may be displayed as a first color (for example, green) or the battery state display part 413 may not blink. On the other hand, in a case where the remaining amount of the battery is less than the reference amount, the color of the battery state display part 413 may be displayed as a second color (for example, red) or the battery state display part 413 may blink.

Meanwhile, as described above, the processor for controlling the overall operation of the skin care device 2 may not be provided in the skin care device 2 but may be provided in the user manipulation device 4. In this case, the processor is connected to the light output module 22 through a cable 421 and thus can control an operation such as a plurality of light sources provided in the light output module 22 and a wear detection sensor 245 provided in the wearing device 24.

Although not illustrated, the user manipulation device 4 may be mounted on the cradle 3 during storage. In this case, the user manipulation device 4 may be connected to the cradle 3 through the connection terminal 422 to receive power from the cradle 3. According to an embodiment, a battery (not illustrated) for supplying power for the operation of the skin care device 2 as well as the user manipulation device 4 may be provided inside the user manipulation device 4. In this case, the battery may be charged by power supplied from the cradle 3. In addition, when the skin care device 2 is operated, the battery may supply power necessary for the operation.

FIG. 5 is a rear view illustrating a light output module of a skin care device according to an embodiment of the present disclosure. FIG. 6 is a rear view illustrating the light output module illustrated in FIG. 5 in more detail.

The rear views illustrated in FIGS. 5 to 6 may correspond to the rear views in which the inner case 23 and the wearing device 24 are removed.

Referring to FIGS. 5 to 6, a plurality of fastening holes 212 for fastening with the inner case 23 are provided on a surface of both surfaces of the outer case 21 which faces the user's skin, when the skin care device 2 is worn. As the outer case 21 and the inner case 23 are fastened through the fastening hole 212 and the fastening member 232, the light output module 22 can be accommodated in a space between the outer case 21 and the inner case 23.

In addition, wearing device fastening parts 213a and 213b to which the wearing device 24 is fastened may be formed in the outer case 21.

Meanwhile, the light output module 22 may include upper modules 222a and 223a disposed on the upper side with respect to the opening 211, and lower modules 222b and 223b disposed on the lower side with respect to the opening 211. However, according to the embodiment, the upper module and the lower module may be implemented integrally.

The upper modules 222a and 223a may include an upper module body 222a that forms a predetermined area, and an upper module cover 223a that is formed along a part of an outer edge of the upper module body 222a. For example, the upper module cover 223a may be positioned between the outer part of the upper module body 222a and the outer peripheral surface of the outer case 21.

Similarly, the lower modules 222b and 223b may include a lower module body 222b that forms a predetermined area, and a lower module cover 223b that is formed along a portion of the outer part of the lower module body 222b. For example, the lower module cover 223b may be positioned between the outer part of the lower module body 222b and the outer peripheral surface of the outer case 21.

A plurality of light sources 2231 may be disposed between the upper module body 222a and the upper module cover 223a and between the lower module body 222b and the lower module cover 223b. The plurality of light sources 2231 may include a visible light LED that emits visible light (for example, red light or the like) and/or an IR LED that emits infrared light.

Each of the plurality of light sources 2231 may be disposed in an array form along the length direction of the upper module cover 223a and the lower module cover 223b. In other words, each of the plurality of light sources 2231 may be disposed in an array form along a portion of the outer part of the upper module body 222a and a portion of the outer part of the lower module body 222b.

Meanwhile, the area of the upper module body 222a and the area of the lower module body 222b may be different from each other. In this case, the number of light sources included in the upper module may be different from the number of light sources included in the lower module. For example, in a case where the area of the upper module body 222a is smaller than the area of the lower module body 222b, the number of light sources included in the upper module may be less than the number of light sources included in the lower module.

Alternatively, in a case where the area of the upper module body 222a is smaller than the area of the lower module body 222b, the output (intensity) of the light source included in the upper module may be smaller than the output of the light source included in the lower module, and the distance between the light sources included in the upper module may be wider than the distance between the light sources included in the lower module.

Each of the plurality of light sources 2231 is not disposed to face the user's skin when the skin care device 2 is worn, but can be disposed to face the center of the skin care device 2 or the region CA including the center. In other words, each of the plurality of light sources 2231 may emit light toward the center or the region CA.

The region CA has a relatively greater distance from the light source 2231 than other regions. Accordingly, the intensity of light irradiated by one light source 2231 may be lower than that of other regions, but since the plurality of light sources 2231 are disposed to face the region CA, the light density of the region CA may be higher than that of other regions. Accordingly, the light intensity deviation between regions of the module body 222a and 222b may be minimized.

Each of the plurality of light sources 2231 may correspond to a point light source. In other words, the intensity (or brightness) of the light emitted from each of the plurality of light sources 2231 may increase as it approaches a specific point, and the intensity (or brightness) thereof decreases as it moves away from the specific point.

The light output module 22 according to an embodiment of the present disclosure may correspond to a surface light source module. To this end, the upper module body 222a and the lower module body 222b may be implemented to transmit the light emitted from the plurality of light sources 2231 to the skin in the surface light-emitting form. Accordingly, the light transmitted to the skin may have no difference in intensity (or brightness) for each point or region or may be less than a reference value. In other words, the light output module 22 may be implemented to evenly irradiate light to each of the user's skin regions.

Structures of the module bodies 222a and 222b and the covers 223a and 223b, and specific details related to the operating principle of the light output module will be described with reference to FIGS. 7 to 8.

FIG. 7 is a schematic cross-sectional view taken in the direction A-A' of FIG. 5. FIG. 8 is a view for explaining an operating principle of the light output module according to the embodiment of FIG. 5.

Referring to FIGS. 7 to 8, the module bodies 222a and 222b may include a reflector 2221 and a light guide panel 2222.

The reflector 2221 and the light guide panel 2222 may be implemented in the form of a plate having a curved surface.

The reflector 2221 may be disposed between the light guide panel 2222 and the outer case 21 to reflect light emitted from the light source 2231 in the direction of the light guide panel 2222.

The reflector 2221 may be implemented as a reflective sheet including various materials that reflect light, but is not limited thereto. According to an embodiment, the surface of the reflector 2221 may form an irregular surface to reflect light emitted from the light source 2231 in various directions.

Meanwhile, the reflector 2221 may have a curved surface that is curved toward the direction in which the light source 2231 is disposed, or may be formed to be inclined at a predetermined angle with respect to the direction in which the light source 2231 is directed. Accordingly, the light emitted from the light source 2231 may be effectively irradiated to the entire region of one surface of the reflector 2221.

The light guide panel (or light guide plate; 2222) may be disposed between the reflector 2221 and the inner case 23. The light guide panel 2222 diffuses the light emitted from the light source 2231 and the light reflected from the reflector 2221 so that the module bodies 222a and 222b function as a surface light source.

The light guide panel 2222 may be made of a light-transmitting material, for example, silicone or acrylic resin, but is not limited thereto and may be made of various resins. According to an embodiment, a plurality of scattering particles may be further included in the light guide panel 2222. The plurality of scattering particles may scatter or refract light, so that light emitted from the light source 2231 and light reflected from the reflector 2221 may be more widely spread.

Meanwhile, as illustrated in FIG. 8, the thickness of the light guide panel 2222 may vary according to a distance from the light source 2231.

Specifically, the first thickness TH1 of the light guide panel 2222 at the position closest to the light source 2231 can be greater than the second thickness TH2 of the light guide panel 2222 at the position furthest away from the light source 2231. In other words, the thickness of the light guide panel 2222 may become smaller as it moves away from the light source 2231.

As the distance to the light source 2231 decreases, the region to which the light emitted from the light source 2231 is irradiated may become narrower. Accordingly, the light guide panel 2222 is formed to be thicker as the distance from the light source 2231 is shorter, so that light can be effectively diffused.

In addition, as the distance from the light source 2231 increases, the region to which the light emitted from the light source 2231 is irradiated may become wider. In other words, since light is diffused to some extent as the distance from the light source 2231 increases, the light may be sufficiently diffused even if the thickness of the light guide panel 2222 is thin. In other words, the light guide panel 2222 is formed thinner as the distance from the light source 2231 increases, so that unnecessary increase in thickness and weight of the light output module 22 can be minimized.

In some embodiments, the light guide panel 2222 and the inner case 23 may be formed to be spaced apart from each other by a predetermined distance. In this case, an air gap region AG is formed between the light guide panel 2222 and the inner case 23, and light passing through the light guide panel 2222 may be further diffused in the air gap region AG. As a result, since the surface light-emittance (SEL) of the light output module 22 is more evenly provided, light of even intensity can be irradiated to the skin regions.

Although not illustrated, one of the surfaces of the light guide panel 2222 facing the inner case 23 may be implemented to form an irregular surface to disperse the light in more various paths.

Meanwhile, the upper module cover 223a and the lower module cover 223b may be formed to surround the plurality of light sources 2231 to protect the plurality of light sources 2231.

For example, each of the upper module cover 223a and the lower module cover 223b may include a first partial cover 2232 disposed between the plurality of light sources 2231 and the inner case 23, and a second partial cover 2233 disposed between the outer case 21 and the plurality of light sources 2231 and fastened to the first partial cover 2232. The plurality of light sources 2231 may be accommodated in a space formed by the first partial cover 2232, the second partial cover 2233, and the light guide panel 2222.

FIG. 9 is a rear view illustrating a light output module of a skin care device according to an embodiment of the present disclosure. FIG. 10 is a cross-sectional view illustrating the light output module illustrated in FIG. 9. FIG. 11 is an exemplary view for explaining an embodiment related to the arrangement of the light source of the light output module illustrated in FIG. 9.

The rear view illustrated in FIG. 9 may correspond to a rear view illustrating a state where the inner case 23 and the wearing device 24 are removed.

Referring to FIGS. 9 to 10, since the fastening hole 212 and the wearing device fastening parts 213a and 213b have been described above with reference to FIGS. 5 to 6, a description thereof will be omitted.

The light output module 22 may include an upper module 226a disposed at an upper side with respect to the opening 211 and a lower module 226b disposed at a lower side thereof. However, according to the embodiment, the upper module and the lower module may be implemented integrally.

Each of the upper module 226a and the lower module 226b may form a predetermined area and may be implemented as a surface light source irradiating light corresponding to the predetermined area to the skin.

Meanwhile, the upper module 226a and the lower module 226b may be implemented to correspond to the shapes of the outer case 21 and the inner case 23. In other words, as the outer case 21 and the inner case 23 are formed to be rounded, the upper module 226a and the lower module 226b may also be formed to be rounded. In this case, the substrate 2266 included in the upper module 226a and the lower module 226b may form a curved surface. To this end, the substrate 2266 may be implemented as an FPCB, but this is not necessarily the case.

Each of the upper module 226a and the lower module 226b may include a plurality of visible light sources 2261. The plurality of visible light sources 2261 may be disposed to be spaced apart from each other by a predetermined distance. For example, the plurality of visible light sources 2261 may be implemented as a red LED emitting red light, but is not limited thereto.

The plurality of visible light sources 2261 may not be disposed to face the user's skin when the skin care device 2 is worn. For example, each of the plurality of visible light sources 2261 may be disposed to face a direction parallel to the substrate 2266. Alternatively, in a case where the substrate 2266 forms a curved surface, each of the plurality of visible light sources 2261 may be disposed to face a tangential direction of the substrate 2266.

As illustrated in FIG. 10, the light output module 22 may be implemented to transmit a plurality of visible light sources 2261 corresponding to point light sources to the skin in the form of surface light emittance (SEL).

To this end, each of the upper module 226a and the lower module 226b may include a light diffusion layer 2263 and a reflector 2265.

The reflector 2265 may be formed on the substrate 2266 to reflect the light irradiated toward the substrate 2266 among the light emitted from the plurality of visible light sources 2261 to the light diffusion layer 2263. For example, the reflector 2265 may be implemented as a reflective sheet including various materials that reflect light, but is not limited thereto. According to an embodiment, the surface of the reflector 2265 may form an irregular surface to reflect light emitted from the light source 2261 in various directions.

The light diffusion layer 2263 may be formed on the reflector 2265 to have a predetermined thickness. The light diffusion layer 2263 may be positioned between the reflector 2265 and the inner case 23.

The light diffusion layer 2263 diffuses the light emitted from the light source 2261 and the light reflected from the reflector 2265, similarly to the light guide panel 2222 described above, so that the upper module 226a and the lower module 226b may function as surface light source.

The light diffusion layer 2263 may be made of a light-transmitting material, for example, silicon, but is not limited thereto and may be made of various resins. According to an embodiment, a plurality of scattering particles may be further included in the light diffusion layer 2263. The plurality of scattering particles may scatter or refract light, so that light emitted from the light source 2261 and light reflected from the reflector 2265 may be more widely spread.

Although not illustrated, one of the surfaces of the light diffusion layer 2263 facing the inner case 23 (the upper surface of the light diffusion layer 2263 in FIG. 10) forms an irregular surface and thus is implemented so as to disperse light in more various paths.

According to the embodiment, a light transmission amount adjusting layer 2264 may be formed on some regions of the upper surface of the light diffusion layer 2263. The partial regions in which the light transmission amount adjusting layer 2264 is formed may correspond to a region within a predetermined distance from each of the plurality of visible light sources 2261. Although it is illustrated in FIG. 10 that the light transmission amount adjusting layer 2264 is formed on the upper surface of the light diffusion layer 2263, the light transmission amount adjusting layer 2264 may be formed on the inner case 23, according to the embodiment.

The light intensity of a region adjacent to the visible light source 2261 may be greater than the light intensity of a region relatively spaced apart from the visible light source 2261. In this case, when the surface light-emittance SEL is provided from the light output module 22, there may be a deviation in the light intensity irradiated for each skin region.

In other words, since the light transmission amount adjusting layer 2264 is formed in a region within a predetermined distance from each of the plurality of visible light sources 2261, the above-described variation in light intensity may be minimized.

For example, the light transmission amount adjusting layer 2264 may be made of various materials that absorb or reflect a portion of light. In other words, some of the light irradiated to the light transmission amount adjusting layer 2264 is transmitted through the light transmission amount adjusting layer 2264 to be irradiated to the skin, and the rest is absorbed or reflected, so that the intensity of light irradiated to the skin may be reduced.

According to an embodiment, each of the upper module 226a and the lower module 226b may further include a plurality of infrared light sources 2262 emitting infrared light. The plurality of infrared light sources 2262 may be disposed to face the user's skin when the skin care device 2 is worn, but this is not necessarily the case, and similar to the plurality of visible light sources 2261, may be disposed to face a direction parallel to the substrate 2266 or a tangential direction. The plurality of infrared light sources 2262 may be implemented as an IR LED, but is not limited thereto.

Meanwhile, the area of the upper module 226a and the area of the lower module 226b may be different from each other. In this case, the number of light sources included in the upper module 226a and the number of light sources 2261 and 2262 included in the lower module 226b may be different from each other. For example, in a case where the area of the upper module 226a is smaller than the area of the lower module 226b, the number of light sources 2261 and 2262 included in the upper module 226a is may be less than the number of light sources 2261 and 2262 included in the lower module 226b.

According to an embodiment, the distance between the light sources disposed in the upper module 226a or the lower module 226b may be different from each other for each region. Alternatively, the intensity of light output from the light sources may be different from each other for each region.

Based on this, the skin care device 2 may be implemented such that the intensity of light irradiated to a predetermined region requiring intensive care among skin regions is greater than the intensity of light irradiated to other regions.

Referring to the example of FIG. 11, the skin care device 2 may be implemented in the form of a mask that can be worn on a person's face, and a forehead region and a cheek region among the person's face regions may correspond to regions requiring intensive care.

When the skin care device 2 is worn, the first region R1 of the upper module 226a corresponds to the wearer's forehead region, and the second region R2 and the third region R3 of the lower module 226b may correspond to the wearer's cheek region. In other words, the light provided from the first region R1 may be irradiated to the wearer's forehead, and the light provided from the second region R2 and the third region R3 may be irradiated to the wearer's cheeks.

In this case, the interval between the plurality of visible light sources 2261 (or the infrared light sources 2262) disposed in the first region R1, the second region R3, and the third region R3 may be formed to be narrower than the interval between the plurality of visible light sources 2261 (or the infrared light sources 2262) disposed in the remaining region. Alternatively, the light output (reference light intensity) of the plurality of visible light sources 2261 (or infrared light sources 2262) disposed in the first region R1, the second region R3, and the third region R3 may be greater than the light output of the plurality of visible light sources 2261 (or infrared light sources 2262) disposed in the remaining region.

In other words, the light sources provided in the skin care device 2 are implemented to provide light of greater intensity to a predetermined region, thereby maximizing the skin care effect.

According to the embodiments illustrated in the FIGS. 5 to 11, the light output module 22 of the skin care device 2 may be implemented with various types of surface light source modules to provide surface light emission type light to the user's skin. Although not illustrated, the light output module 22 may be implemented as an OLED panel, a microLED panel, or the like of a predetermined size to provide surface-emitting light to the user's skin.

FIGS. 12a to 12c are experimental data for explaining a change in a light reduction rate according to a separation distance for a point light source and a surface light source, respectively. FIG. 13a is an exemplary view illustrating the intensity of light irradiated to skin regions when a skin care device equipped with a point light source is used, and FIG. 13b is an exemplary view illustrating the intensity of light irradiated to the skin regions when a skin care device equipped with a surface light source is used.

As described above, the point light source is a light source that intensively irradiates light to a predetermined point, and as the point light source is closer to the predetermined point, the intensity (or brightness) increases, and as the point light source is farther away from the predetermined point, the intensity (or brightness) decreases. The surface light source is a light source that uniformly irradiates light to the entire predetermined region and may have no difference in intensity (or brightness) for each point or region or may be less than a reference value.

The intensity of the light emitted from the point light source may decrease rapidly as the distance from the point light source increases. On the other hand, the light emitted from the surface light source may have a low rate of decrease in intensity compared to the point light source when the separation distance from the surface light source increases.

Specifically, referring to the experimental data of FIGS. 12a to 12b, it can be confirmed that, in the case of the point light source, the light intensity is reduced by about 52.9% even though the point light source is spaced apart only by 5 mm. In other words, the light intensity at a separation distance of 5 mm is only about 47.1% of the reference light intensity (light intensity at the position where the distance is 0) of the point light source. In addition, it can be checked that the intensity of light irradiated at a distance of 10 mm is reduced by about 76.5% compared to the reference light intensity.

On the other hand, in the case of a surface light source, it can be checked that the intensity of light irradiated at a separation distance of 5 mm is reduced by about 22.5% compared to the reference light intensity, and the intensity of light irradiated at a separation distance of 10 mm is reduced by about 47.3% compared to the reference light intensity.

In other words, in the case of the surface light source, it can be seen that the deviation of the light intensity according to the separation distance from the light source is relatively lower than that of the point light source.

Based on this, referring to FIG. 12c, in the case of a point light source, as the separation distance increases, the light intensity rapidly decreases. Accordingly, in order to provide light having a preset intensity for skin care, the reference light intensity of the point light source should be several times greater than the preset light intensity.

On the other hand, in the case of a surface light source, the degree of decrease in light intensity according to an increase in the separation distance is relatively smaller than that of a point light source. Accordingly, the surface light source can sufficiently provide the light of the predetermined intensity to the skin even though the surface light source has a reference light intensity smaller than the reference light intensity of the point light source. In other words, the power consumption and efficiency of the skin care device irradiating light to the skin through the surface light source may be superior to the power consumption and efficiency of the conventional skin care device irradiating light to the skin through the point light source.

Meanwhile, referring to FIGS. 13a to 13b, the distance between the skin care device and the skin may have various ranges according to the wearing part.

When the skin care device is implemented in the form of a mask worn on a person's face, the distance between the skin care device and the face may vary greatly according to a portion of the face (for example, in a range of about 15 mm to 30 mm). For example, the distance between the skin care device and the nose may be much shorter than the distance between the skin care device and the forehead.

In a case where a skin care device having a point light source as illustrated in FIG. 13a is worn on the face and irradiates light to the skin, the light irradiated from the point light source has a relatively large variation in light intensity according to the separation distance, and thus there may be a large difference between the intensity of the light irradiated to the nose and cheeks (cheekbones) and the intensity of the light irradiated to the forehead or the chin. In other words, since light of sufficient intensity is not irradiated to the forehead or chin, sufficient skin care efficacy for the forehead or chin may not be provided. Alternatively, excessive intensity of light is irradiated to the nose and cheeks, and side effects (trouble, burns, or the like) may occur in skin regions corresponding to the nose and cheeks.

On the other hand, in a case where a skin care device having a surface light source as illustrated in FIG. 13b is worn on the face and irradiates light to the skin, the light irradiated from the surface light source has a relatively small variation in light intensity according to the separation distance, and thus it can be seen that the deviation of the intensity of light irradiated to each of the face parts is very low compared to FIG. 13a. Accordingly, sufficient skin care efficacy for each of the face parts may be provided, and the occurrence of side effects due to excessive light intensity being irradiated to a specific part may be prevented.

In other words, the skin care device according to an embodiment of the present disclosure irradiates light to the skin using a surface light source, and thus the deviation of the light intensity due to the distance deviation is minimized, thereby easily providing a uniform care efficacy for each skin part.

In addition, since the skin care device having a surface light source according to an embodiment of the present disclosure can provide light with a greater intensity to the skin even with a lower reference light intensity than a conventional skin care device having a point light source, it can maximize efficiency compared to skin care devices of the prior art.

The above description is merely illustrative of the technical spirit of the present disclosure, and various modifications and variations will be possible without departing from the essential characteristics of the present disclosure by those skilled in the art to which the present disclosure pertains.

Therefore, the embodiments disclosed in the present disclosure are not intended to limit the technical spirit of the present disclosure, but to explain, and the scope of the technical spirit of the present disclosure is not limited by these embodiments.

The protection scope of the present disclosure should be construed by the following claims, and all technical ideas within the scope equivalent thereto should be construed as being included in the scope of the present disclosure.

The invention claimed is:

1. A skin care device comprising:
an outer case having a first opening;
an inner case configured to be fastened to the outer case and having a second opening corresponding to the first opening; and
a light output device configured to be accommodated between the outer case and the inner case,
wherein the light output device includes:
a body configured to form a predetermined area based on a shape of the outer case or the inner case, wherein the body includes a light guide panel having the predetermined area;
a cover located along a part of an outer part of the body; and
a plurality of light sources disposed between the body and the cover in a form of an array along the outer part of the body, and
wherein each of the plurality of light sources is disposed to face the body,
wherein the cover includes:
a first partial cover located between the plurality of light sources and the inner case; and
a second partial cover located between the plurality of light sources and the outer case and fastened to the first partial cover, and
wherein an accommodation space accommodating the plurality of light sources is located between the first partial cover, the second partial cover, and the light guide panel.

2. The skin care device of claim 1,
wherein each of the plurality of light sources is disposed to face a center of the skin care device or a region of a predetermined size including the center.

3. The skin care device of claim 1,
wherein the body further includes:
a reflector disposed between the light guide panel and the outer case,
wherein the light guide panel is configured to diffuse and transmit light emitted from the plurality of light sources and light reflected from the reflector to the inner case, and
wherein the reflector has a curved surface facing a direction in which the plurality of light sources are disposed, or a surface inclined at a predetermined angle with respect to the direction in which the plurality of light sources are disposed.

4. The skin care device of claim 3,
wherein the light guide panel has different thicknesses according to a separation distance from the plurality of light sources.

5. The skin care device of claim 4,
wherein a first thickness of the light guide panel at a portion separated from the plurality of light sources by a first distance is greater than a second thickness of the light guide panel corresponding to a portion separated from the plurality of light sources by a second distance greater than the first distance.

6. The skin care device of claim 3,
wherein the light guide panel is spaced apart from the inner case by a predetermined distance.

7. The skin care device of claim 3,
wherein a surface of the light guide panel or a surface of the reflector forms an irregular surface.

8. The skin care device of claim 3,
wherein the light guide panel is composed of silicone or acrylic resin.

9. The skin care device of claim 1,
wherein the light output device includes:
an upper module located at an upper side with respect to the first opening or the second opening; and
a lower module located at a lower side with respect to the first opening or the second opening, wherein a third opening corresponding to the first opening or the second opening is located between the upper module and the lower module.

10. The skin care device of claim 9, further comprising:
a wearing device configured to be fastened to correspond to the first opening, the second opening and the third opening.

11. The skin care device of claim 1,
wherein the inner case is transparent or translucent.

* * * * *